US00PP29568P3

(12) United States Plant Patent
Robb

(10) Patent No.: US PP29,568 P3
(45) Date of Patent: Jul. 31, 2018

(54) ***LAVANDULA* PLANT NAMED 'LAMPU31-0'**

(50) Latin Name: *Lavandula stoechas*
Varietal Denomination: LAMPU31-0

(71) Applicant: John Robb, Kariong (AU)

(72) Inventor: John Robb, Kariong (AU)

(73) Assignee: Paradise Seed Co. Pty, Ltd. (AU)

( * ) Notice: Subject to any disclaimer, the term of this patent is extended or adjusted under 35 U.S.C. 154(b) by 0 days.

(21) Appl. No.: 15/330,626

(22) Filed: Oct. 18, 2016

(65) Prior Publication Data

US 2018/0110169 P1 Apr. 19, 2018

(51) Int. Cl.
*A01H 5/02* (2018.01)

(52) U.S. Cl.
USPC ..... Plt./445
CPC ..... *A01H 5/02* (2013.01)

(58) Field of Classification Search
USPC ..... Plt./445
See application file for complete search history.

*Primary Examiner* — Susan McCormick Ewoldt
(74) *Attorney, Agent, or Firm* — Cassandra Bright

(57) ABSTRACT

A new and distinct *Lavandula* cultivar named 'LAMPU31-0' is disclosed, characterized by long inflorescences composed of light purple infertile bracts and dark purple flowers. Plants begin flowering and are distinctively upright in habit and resist lodging. The new variety is a *Lavandula*, normally produced as an outdoor garden or container plant.

1 Drawing Sheet

Latin name of the genus and species: *Lavandula stoechas*.
Variety denomination: 'LAMPU31-0'.

BACKGROUND OF THE INVENTION a product of a planned breeding program conducted by the inventor, John Robb, in New South Wales, Australia. The objective of the breeding program was to produce new Lavender varieties for ornamental commercial applications. The open pollination resulting in this new variety was made during October of 2009.

The seed parent is *Lavandula* 'Bee Brilliant', U.S. Plant Pat. No. 12,614. The pollen parent is unknown as it was an open pollination breeding program, using several proprietary pollen parents. The new variety was discovered in October of 2011 by the inventor in a group of seedlings resulting from the 2009 crossing, in a research greenhouse in New South Wales, Australia.

Asexual reproduction of the new cultivar was performed by vegetative terminal cuttings. This was first performed at a research greenhouse in New South Wales, Australia during January of 2012 and has shown that the unique features of this cultivar are stable and reproduced true to type in at least 4 successive generations.

SUMMARY OF THE INVENTION

The cultivar 'LAMPU31-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LAMPU31-0' These characteristics in combination distinguish 'LAMPU31-0' as a new and distinct *Lavandula* cultivar:

1. Early flowering.
2. Long infertile bracts.
3. Upright plant form.
4. Strong plant habit, resists lodging.
5. Dark purple fertile flowers and lighter purple infertile bracts.

Plants of the new cultivar 'LAMPU31-0' are similar to plants of the seed parent, *Lavandula stoechas* 'Bee Brilliant' in most horticultural characteristics, however, plants of the new cultivar 'LAMPU31-0' differ in the following:

1. The new variety produces lighter purple infertile bracts.
2. The infertile bracts of the new variety are longer and less undulating than those of the seed parent.
3. Plant habit of the new variety is more upright.
4. The new variety is a stronger plant, resisting lodging better than the seed parent.

COMMERCIAL COMPARISON

Plants of the new cultivar 'LAMPU31-0' are comparable to the variety *Lavandula* 'Voodoo', U.S. Plant Pat. No. 25,739. The two *Lavandula* varieties are similar in most horticultural characteristics; however, the new variety 'LAMPU31-0' differs in producing shorter infertile bracts, which are held upright, not at a wider angle. Peduncles of the new variety are shorter. Additionally plants of 'LAMPU31-0' are shorter and more upright than this comparator.

Plants of the new cultivar 'LAMPU31-0' are comparable to the variety *Lavandula* 'Larkman Bee', U.S. Plant Pat. No. 20,840. The two *Lavandula* varieties are similar in most horticultural characteristics; however, the new variety 'LAMPU31-0' differs in producing longer infertile bracts. Additionally plants of 'LAMPU31-0' are more upright than this comparator.

Plants of the new cultivar 'LAMPU31-0' can also be compared to the commercial variety *Lavandula* 'Larkman Hazel' U.S. Plant Pat. No. 20,894. These varieties are similar in most horticultural characteristics however, the new variety 'LAMPU31-0' differs in producing longer overall inflorescence, shorter infertile bracts, shorter peduncles than the comparator. Additionally plants of 'LAMPU31-0' are more upright than the comparator and produce more inflorescence per plant.

BRIEF DESCRIPTION OF THE PHOTOGRAPH

The accompanying photograph illustrates in full color a typical plant of 'LAMPU31-0' grown outdoors in Santa Paula, Calif. The prominent plant in the foreground, with light purple bracts is 'LAMPU31-0'. Age of the plant photographed is approximately 40 weeks from a rooted cutting. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'LAMPU31-0' plants grown outdoors during, Winter and Spring in Santa Paula, Calif. The growing temperature ranged from 10° C. to 35° C. during the day and from 5° C. to 25° C. during the night. General light conditions are bright, normal sunlight. Measurements and numerical values represent averages of typical plant types.

Botanical classification: *Lavandula stoechas* 'LAMPU31-0'.

PROPAGATION

Time to initiate roots: About 10 to 14 days at approximately 21° C.

Time to produce a rooted cutting: About 25 to 35 days at 21° C.

PLANT

Age of plant described: Approximately 9 months from an unrooted cutting.

Plant spread: Approximately 35 cm.

Plant height: Approximately 46 cm, to top of flowering plane. Approximately 27 cm to top of foliar plane.

Growth rate: Moderate to rapid.

Length of primary lateral branches: Approximately 17 cm.

Diameter of lateral branches: Approximately 0.35 cm.

Quantity of lateral branches: About 30.

Plant habit: Moderately dense, upright.

Stem:

- *Juvenile color*.—Near Greyed-Yellow 160C, ridges striped Green 143B, irregular flush near Greyed-Purple 187A.
- *Mature color*.—Near Brown 200C, with oldest woody stems also Brown 200C.
- *Texture*.—Puberulent.

Internode length: Average 1.5 cm.

FOLIAGE

Leaf:

- *Arrangement*.—2 large opposite leaves at each node.
- *Leaf type*.—Simple.
- *Quantity*.—Average 18 fully expanded per main branch.
- *Average length*.—Average 2.9 (mature foliage).
- *Average width*.—Average 0.35 cm. (mature foliage).
- *Shape of blade*.—Lanceolate.
- *Apex*.—Acute.
- *Base*.—Truncate.
- *Attachment*.—Sessile.
- *Margin*.—Entire.
- *Texture of all surfaces*.—Puberbulent.
- *Leaf fragrance*.—Moderately strong Lavender scent.
- *Color*.—Young foliage upper side: Near RHS Green 138C. Young foliage under side: Near Green RHS 138B. Mature foliage upper side: Near RHS Green 137C. Mature foliage under side: Near Green 138A.
- *Venation*.—Type: Reticulate. Venation color upper side: Indistinguishable from foliage color. Venation color under side: Near Green 138B.
- *Petiole*.—Absent.

FLOWER

Bloom period: Main flush during Spring. Lesser quantities of flowers produced throughout Summer and Fall. During peak flowering total inflorescence quantity between 70 and 100 per plant.

Inflorescence:

- *Form*.—Small single flower in verticillasters arranged in spikes. Most commonly 8 rows of flowers. Infrequently 6 or 10 rows. Flowers have small bracts, and large showy terminal bracts. Number of individual flowers per spike: Average 80. Fragrance: Very strong lavender scent. Corolla shape: Salverform. Petal Number: 5. Petals Fused or Unfused: Fused at base. Petal Shape: Top 2 lobes obovate, lower 3 lobes ovate. Petal Margin: Entire. Petal Surfaces: Glabrous. Length: Approximately 0.8 cm. (corolla tube and petals). Diameter: Approximately 0.5 cm at widest opening of petals.
- *Inflorescence size, excluding terminal bracts*.—Length: Approximately 4.5 cm. Width: Approximately 1.7 cm. Shape: Cylindrical. Coloration of individual flowers, excluding terminal bracts: Immature: Near Violet-Blue N92B. Mature: Near Violet-Blue N89A, but darker. Fading: Near Greyed-Purple N186. Calyx Width: 0.3 cm. Calyx Length: 0.5 cm. Calyx Shape: Flattened tube. Calyx color: RHS Greyed-Green 191A flushed Violet-Blue N92A. Bract shape: Deltoid. Bract apex: Acute. Bract Color: Lower Surface: Near Yellow-Green 145C , with apex colored Violet-Blue N92A. Upper Surface: Near Yellow-Green 145C , with apex colored Violet-Blue N92A.

Terminal bracts (sterile):

- *Quantity*.—4 per inflorescence.

Large bracts:

- *Attitude and angle of attachment*.—Bracts arising at approximately 15 degree angle from the top of the inflorescence.
- *Length*.—Approximately 2.0 cm.
- *Width*.—Approximately 0.5 cm.
- *Form*.—Petaloid.
- *Margin*.—Entire and slightly undulating.
- *Surface*.—Smooth.
- *Appearance*.—Matte.
- *Shape*.—Oblanceolate.
- *Apex*.—Acute.
- *Base*.—Attenuate.
- *Vein pattern*.—Reticulate.
- *Duration on plant*.—Approximately 12 weeks, with good color. Persistent.
- *Color*.—Upper side of immature bract: Near RHS Purple-Violet N82D, veins 83B. Under side of immature bract: Near RHS Purple-Violet N82C, veins 83B. Upper side of mature bract: Near RHS Purple-Violet N82B, veins 83B. Under side of mature bract: Near RHS Purple-Violet N82A, veins 83B. Bract color fading to: Near RHS Purple-Violet N82A, veins 83B.

Bud:

*Length*.—Approximately 0.6 cm.
*Diameter*.—Approximately 0.4 cm.
*Shape*.—Ovate.
*Color*.—Near RHS Near Violet-Blue N92B.
*Rate of opening*.—Varies with climactic conditions; Approximately 1 week from colored bud to open flower.

Peduncle:

*Peduncle length*.—Average range approximately 2.5 to 6 cm.
*Peduncle diameter*.—Approximately 0.2 cm.
*Aspect*.—Straight to slightly undulating.
*Color*.—Near RHS Yellow-Green 145A.

REPRODUCTIVE ORGANS

Androecium: Extremely reduced, frequently not present.

*Stamens*.—4.
*Anther shape*.—Linear.
*Anther length*.—Approximately 0.5 mm.
*Anther color*.—Near RHS White N155A.
*Pollen quantity*.—Pollen production not observed.

Pistil:

*Number*.—1.
*Length*.—Approximately 3 mm.
*Style*.—Length: Approximately 0.2 cm. Color: Near RHS White N155A.
*Stigma*.—Shape: Globular. Color: Near RHS Violet-Blue N92A. Ovary: Minute and immeasurable.

OTHER CHARACTERISTICS

Seeds and fruits: Seed production not observed to date.

Disease/pest resistance: Neither resistance nor susceptibility to the normal diseases and pests of *Lavandula stoechas*. has been observed.

Drought tolerance and cold tolerance: Hardy perennial. Tolerates high temperature to at least 32° C. Tolerates low temperatures to −5° C. While specific drought tolerance has not been observed, once plants are established very little water is necessary to maintain plants.

What is claimed is:

1. A new and distinct cultivar of *Lavandula* plant named 'LAMPU31-0' as herein illustrated and described.

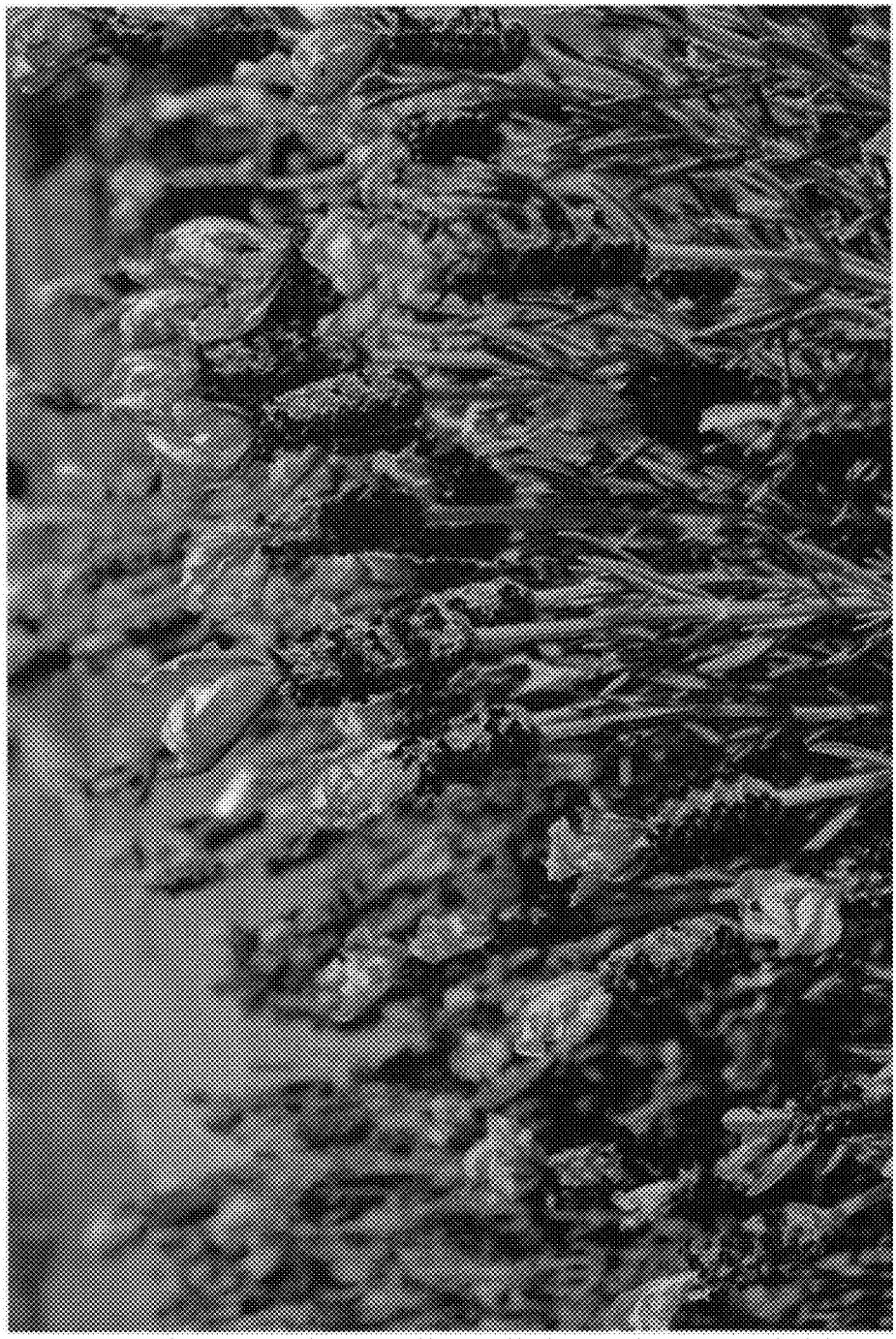

* * * * *